United States Patent
Lupotti et al.

(10) Patent No.: US 11,941,754 B2
(45) Date of Patent: Mar. 26, 2024

(54) SYSTEM AND METHOD FOR GENERATING THREE DIMENSIONAL GEOMETRIC MODELS OF ANATOMICAL REGIONS

(71) Applicant: St. Jude Medical, Cardiology Division, Inc., St. Paul, MN (US)

(72) Inventors: Fermin Lupotti, Lake Forest, CA (US); Anthony Wendling, Watertown, MN (US); Alexander Gorovoy, Kiryat Motzkin (IL); Alon Izmirli, Ganot Hadar (IL); Itai Winkler, Nofit (IL)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 14 days.

(21) Appl. No.: 17/254,953

(22) PCT Filed: Jul. 22, 2019

(86) PCT No.: PCT/US2019/042831
§ 371 (c)(1),
(2) Date: Dec. 22, 2020

(87) PCT Pub. No.: WO2020/055506
PCT Pub. Date: Mar. 19, 2020

(65) Prior Publication Data
US 2021/0217232 A1   Jul. 15, 2021

Related U.S. Application Data

(60) Provisional application No. 62/730,306, filed on Sep. 12, 2018.

(51) Int. Cl.
*G06T 17/00* (2006.01)
*A61B 8/00* (2006.01)
(Continued)

(52) U.S. Cl.
CPC .......... *G06T 17/00* (2013.01); *A61B 8/0883* (2013.01); *A61B 8/12* (2013.01); *A61B 8/466* (2013.01); *A61B 8/5246* (2013.01); *G06T 11/008* (2013.01)

(58) Field of Classification Search
CPC ... G06T 17/00; G06T 11/008; G06T 2210/41; G06T 19/00; A61B 8/0883; A61B 8/12; A61B 8/466; A61B 8/5246
(Continued)

(56) References Cited

U.S. PATENT DOCUMENTS 5,697,377 A   12/1997  Wittkampf
5,983,126 A   11/1999  Wittkampf
(Continued)

FOREIGN PATENT DOCUMENTS

| EP | 3 025 650 | 6/2016 |
|---|---|---|
| WO | 2009/018649 | 2/2009 |
| WO | 2018/086667 | 5/2018 |

OTHER PUBLICATIONS

Ohbuchi et al. (1992) "Incremental vol. reconstruction and rendering for 3-D ultrasound imaging." Proc. SPIE 1808, Visualization in Biomedical Computing, pp. 312-323, 1992 (Year: 1992).*
(Continued)

*Primary Examiner* — James A Thompson
*Assistant Examiner* — Kim Thanh T Tran
(74) *Attorney, Agent, or Firm* — Wiley Rein LLP

(57) ABSTRACT

A three-dimensional geometric model of a heart can be generated from a plurality of two-dimensional image slices of the heart collected using an intracardiac echocardiography ("ICE") catheter. Each image slice can be associated with localization information for the ICE catheter. The image slices can be output in a plurality of voxels according to their associated localization information, thereby creating
(Continued)

a three-dimensional geometric model of the heart. Data sufficiency of the three-dimensional model can also be graphically represented. For example, data sufficiency can be represented using voxel opacity, a one-dimensional illustration, a two-dimensional illustration, and/or a data collection cue.

15 Claims, 7 Drawing Sheets

(51) Int. Cl.
  *A61B 8/08* (2006.01)
  *A61B 8/12* (2006.01)
  *G06T 11/00* (2006.01)
(58) Field of Classification Search
  USPC .......................................................... 345/424
  See application file for complete search history.

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 2008/0051660 A1* | 2/2008 | Kakadaris ............... A61B 8/481 600/454 |
| 2008/0123921 A1* | 5/2008 | Gielen ...................... G06T 7/73 382/175 |
| 2011/0137156 A1* | 6/2011 | Razzaque ............... A61B 34/20 600/424 |
| 2012/0165664 A1 | 6/2012 | Hill et al. |
| 2013/0169640 A1* | 7/2013 | Sakuragi ................. G06T 15/20 345/419 |
| 2014/0228714 A1* | 8/2014 | Chau .................... A61B 5/7267 600/593 |
| 2014/0330121 A1* | 11/2014 | Kim ....................... A61B 8/485 600/438 |
| 2015/0182191 A1* | 7/2015 | Caluser ................ A61B 5/4312 600/407 |
| 2019/0362548 A1* | 11/2019 | Hatanaka ................ G06T 7/149 |

OTHER PUBLICATIONS

International Search Report and Written Opinion for PCT/US2019/042831, dated Oct. 15, 2019.

* cited by examiner

SYSTEM AND METHOD FOR GENERATING THREE DIMENSIONAL GEOMETRIC MODELS OF ANATOMICAL REGIONS

CROSS-REFERENCE TO RELATED APPLICATIONS

This application claims the benefit of U.S. provisional application No. 62/730,306, filed 12 Sep. 2018, which is hereby incorporated by reference as though fully set forth herein.

BACKGROUND

The instant disclosure relates to imaging, including medical imaging. In particular, the instant disclosure relates to apparatuses, systems, and methods for generating three-dimensional geometric models of anatomical regions.

Ultrasound transducers are utilized in a variety of medical applications. In many applications, the transducer is mounted in a catheter that can be navigated through a patient's vasculature and/or body organs to a site of interest.

One such application is intracardiac echocardiography ("ICE"), which utilizes ultrasound to generate a three-dimensional volumetric image of a subject's heart from a plurality of two-dimensional ultrasound images. When creating such a volumetric image, however, it is desirable to collect sufficient data covering the entire region of interest (e.g., regions of clinical importance), including considerations related to cardiac and/or respiration cycles.

BRIEF SUMMARY

Disclosed herein is a method of generating a three-dimensional geometric model of an anatomical region. The method includes: defining a three-dimensional voxel space including a plurality of voxels; receiving a plurality of two-dimensional echographic image slices of the anatomical region, wherein each image slice of the plurality of image slices is associated with localization information; assembling the plurality of two-dimensional echographic image slices of the anatomical region into a three-dimensional geometric model of the anatomical region using the associated localization information; graphically outputting the three-dimensional geometric model of the anatomical region in the three-dimensional voxel space; and graphically representing data sufficiency of the three-dimensional geometric model of the anatomical region. The method can also include outputting guidance (e.g., graphical, audible, and/or haptic feedback) to a practitioner in order to guide the practitioner to collect additional image data that will improve data sufficiency within at least a portion of the three-dimensional geometric model of the anatomical region.

In aspects of the disclosure, the plurality of two-dimensional echographic image slices of the anatomical region can be a plurality of B-mode ultrasound images of the anatomical region. In other aspects of the disclosure, the plurality of two-dimensional echographic image slices of the anatomical region can be a plurality of Doppler ultrasound images of the anatomical region.

According to embodiments disclosed herein, the step of graphically representing data sufficiency of the three-dimensional geometric model of the anatomical region can include representing the data sufficiency of the three-dimensional geometric model of the anatomical region using voxel opacity. For instance, for a selected voxel of the plurality of voxels, an opacity of the selected voxel can increase as data sufficiency at the selected voxel increases and decrease as data sufficiency at the selected voxel decreases.

In other embodiments disclosed herein, the step of graphically representing data sufficiency of the three-dimensional geometric model of the anatomical region can include outputting a one-dimensional illustration of the data sufficiency of the three-dimensional geometric model. For instance, the one-dimensional illustration of the data sufficiency of the three-dimensional geometric model can represent data sufficiency of the three-dimensional geometric model relative to angular orientation of the plurality of echographic image slices.

In still further embodiments disclosed herein, the step of graphically representing data sufficiency of the three-dimensional geometric model of the anatomical region can include outputting a two-dimensional illustration of the data sufficiency of the three-dimensional geometric model. For instance, the two-dimensional illustration of the data sufficiency of the three-dimensional geometric model can represent data sufficiency of the three-dimensional geometric model relative to localization of the plurality of echographic image slices.

It is also contemplated that the step of graphically representing data sufficiency of the three-dimensional geometric model of the anatomical region can include outputting a data collection cue.

Also disclosed herein is a method of generating a three-dimensional geometric model of a heart, including the steps: receiving a plurality of two-dimensional image slices of the heart from an intracardiac echocardiography ("ICE") catheter, wherein each image slice of the plurality of image slices is associated with localization information of the ICE catheter; graphically outputting the plurality of two-dimensional image slices in a plurality of voxels according to the associated localization information of the ICE catheter, thereby creating a three-dimensional geometric model of the heart; and graphically representing data sufficiency of the three-dimensional geometric model of the heart.

For instance, the step of graphically representing data sufficiency of the three-dimensional geometric model of the heart can include representing data sufficiency at a selected voxel of the plurality of voxels using opacity of the selected voxel; representing data sufficiency of the three-dimensional geometric model of the heart using a one-dimensional illustration of data sufficiency relative to angular rotation of the ICE catheter; representing data sufficiency of the three-dimensional geometric model of the heart using a two-dimensional illustration of data sufficiency relative to localization of the ICE catheter; and/or outputting a data collection cue. The data collection cue, in turn, can be responsive to a rotational speed of the ICE catheter.

The instant disclosure also provides a system for generating a three-dimensional geometric model of a heart, including an imaging and modeling module. The imaging and modeling module is configured to: receive a plurality of two-dimensional image slices of the heart from an intracardiac echocardiography ("ICE") catheter, wherein each image slice of the plurality of image slices is associated with localization information of the ICE catheter; graphically output the plurality of two-dimensional image slices in a plurality of voxels according to the associated localization information of the ICE catheter, thereby creating a three-dimensional geometric model of the heart; and graphically represent data sufficiency of the three-dimensional geometric model of the heart, using, for example, voxel opacity, a one-dimensional illustration, a two-dimensional illustration, and/or a data collection cue. The imaging and modeling module can further be configured to provide guidance to a practitioner, such as by visual, audible, and/or haptic feedback, to collect additional image data that increases data sufficiency within at least a portion of the three-dimensional geometric model of the heart.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for the creation of three-dimensional geometric models of anatomical regions. For purposes of illustration, aspects of the disclosure will be described in detail herein with reference to the creation of a three-dimensional geometric model of a patient's heart via intracardiac echocardiography ("ICE"). It is contemplated, however, that the apparatuses, systems, and methods described herein can be used in other contexts, including, without limitation, intravascular ultrasound ("IVUS") devices.

Figure 1:
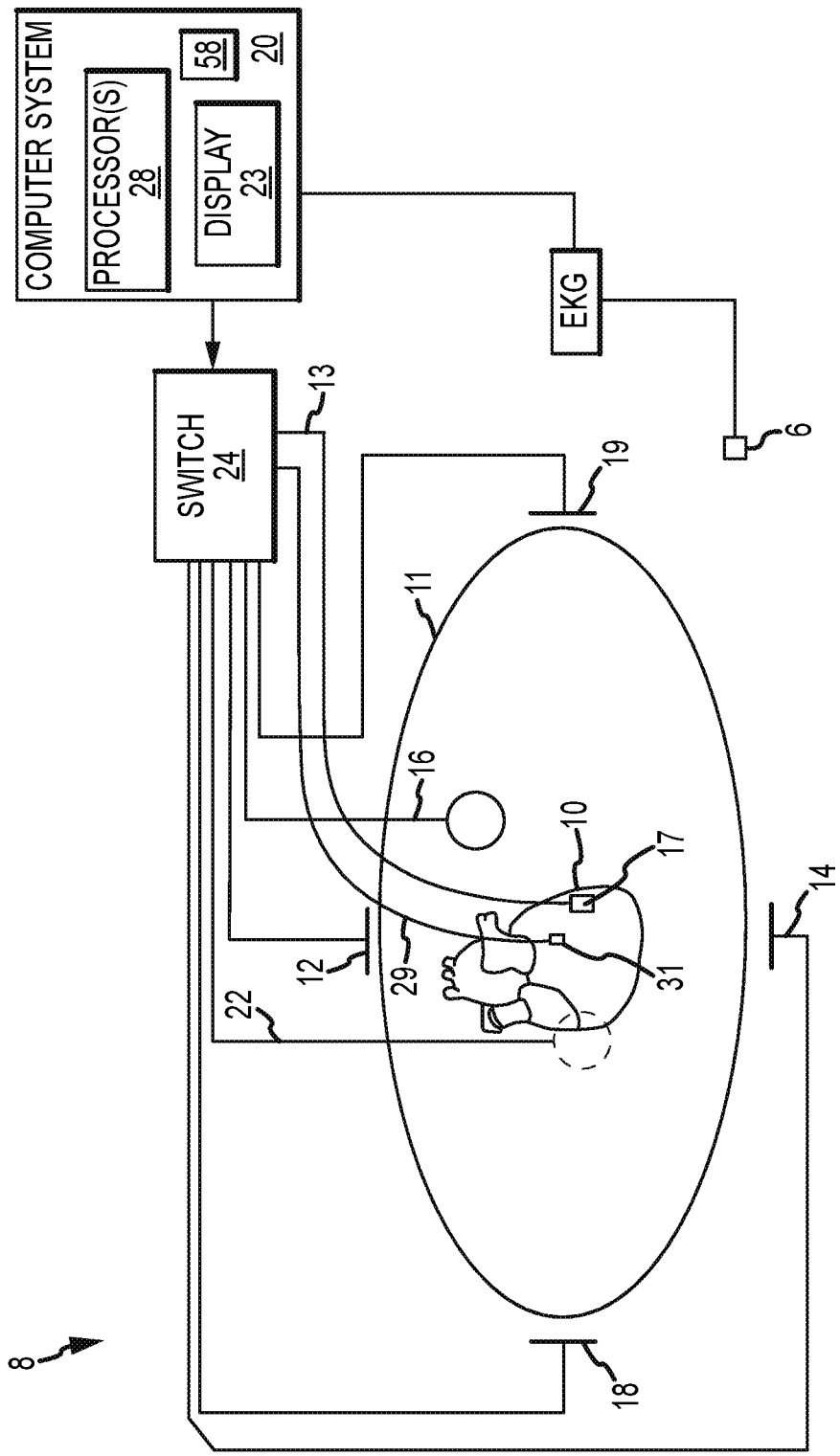
FIG. 1 schematically depicts a system for generating a three-dimensional geometric model of an anatomical region according to aspects of the instant disclosure.

FIG. 1 is a schematic diagram of an exemplary system 8 for generating a three-dimensional geometric model of, for example, a patient's heart. As one of ordinary skill in the art will recognize, and as will be further described below, system 8 determines the location, and in some aspects the orientation, of objects, typically within a three-dimensional space, and expresses those locations as position information determined relative to at least one reference.

In some embodiments, system 8 is the EnSite Precision™ cardiac mapping system of Abbott Laboratories (Abbott Park, Ill.). Other localization systems, however, may be used in connection with the present teachings, including for example the RHYTHMIA HDX™ mapping system of Boston Scientific Corporation (Marlborough, Mass.), the CARTO navigation and location system of Biosense Webster, Inc. (Irvine, Calif.), the AURORA® system of Northern Digital Inc. (Waterloo, Ontario), and Sterotaxis, Inc.'s (St. Louis, Mo.) NIOBE® Magnetic Navigation System.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The foregoing systems, and the modalities they employ to localize a medical device, will be familiar to those of ordinary skill in the art. For purposes of explanation, system 8 will be described herein in the context of magnetic localization, and will only be described herein to the extent necessary to facilitate an understanding of the instant disclosure by one of ordinary skill in the art.

For simplicity of illustration, the patient 11 is depicted schematically as an oval. In the embodiment shown in FIG. 1, magnetic field generators 12, 14, 16, 18, 19, and 22 are located external to patient 11, thereby defining three generally orthogonal axes, referred to herein as an x-axis, a y-axis, and a z-axis. The patient's heart 10 lies within the magnetic field generated by magnetic field generators 12, 14, 16, 18, 19, and 22.

Patient 11 may also have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity of illustration, only a single lead 6 and its connection to computer 20 is shown in FIG. 1.

An ultrasound imaging catheter 13 is also shown schematically in FIG. 1. In aspects of the disclosure, catheter 13 can be an ultrasonic echocardiography (ICE) catheter similar to Abbott Laboratories' ViewFlex™ Xtra ICE catheter. Catheter 13 further includes a sensor 17 to sense the magnetic fields generated by magnetic field generators 12, 14, 16, 18, 19, and 22.

Returning now to FIG. 1, in some embodiments, a fixed reference 31 (e.g., attached to a wall of the heart 10) is shown on a second catheter 29. Often, reference 31 is placed in the coronary sinus and defines the origin of a coordinate system with reference to which catheter 13 is localized by system 8.

Computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Amongst other things, computer system 8 can interpret measurements by sensor 17 of the magnetic fields generated by magnetic field generators 12, 14, 16, 18, 19, and 22 to determine the position and orientation of catheter 13 within heart 10. The term "localization" is used herein to describe the determination of the position and orientation of an object, such as catheter 13, within the magnetic fields created by magnetic field generators 12, 14, 16, 18, 19, and 22.

Aspects of the disclosure relate to the creation of three-dimensional models of cardiac geometry from echographic imagery captured, for example, by catheter 13. Accordingly, system 8 can also include an imaging and modeling module 58.

Figure 6:
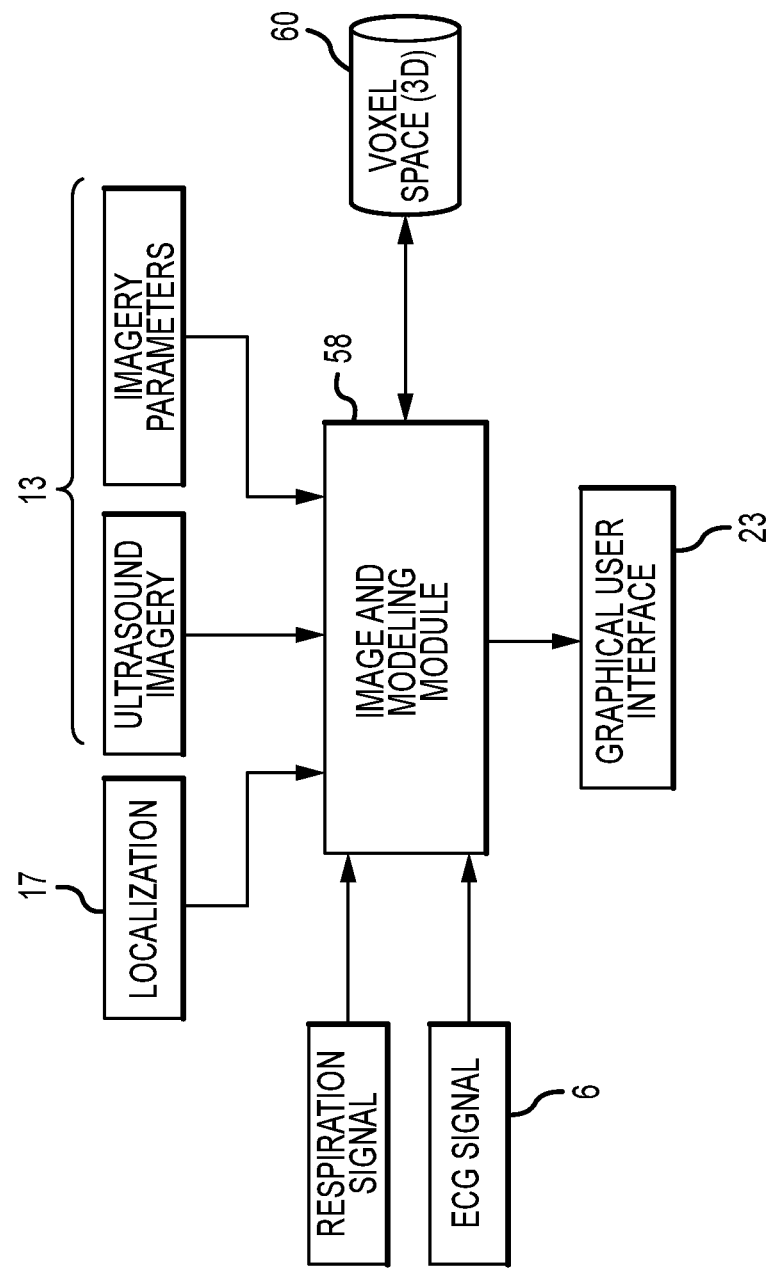
FIG. 6 is a block diagram showing inputs and outputs from an imaging and modeling module as disclosed herein.

FIG. 6 is a block diagram of imaging and modeling module 58 and its inputs and outputs according to aspects disclosed herein. As discussed in detail below, imaging and modeling module 58 can synthesize localization data (e.g., of sensor 17 carried by catheter 13) with ultrasound imagery parameters and data (e.g., from catheter 13) into a three-dimensional voxel space 60 that can be graphically output (e.g., on display 23). Imaging and modeling module 58 can also synthesize ECG and/or respiration data (e.g., to gate the collection of localization and imagery information).

Figure 2:
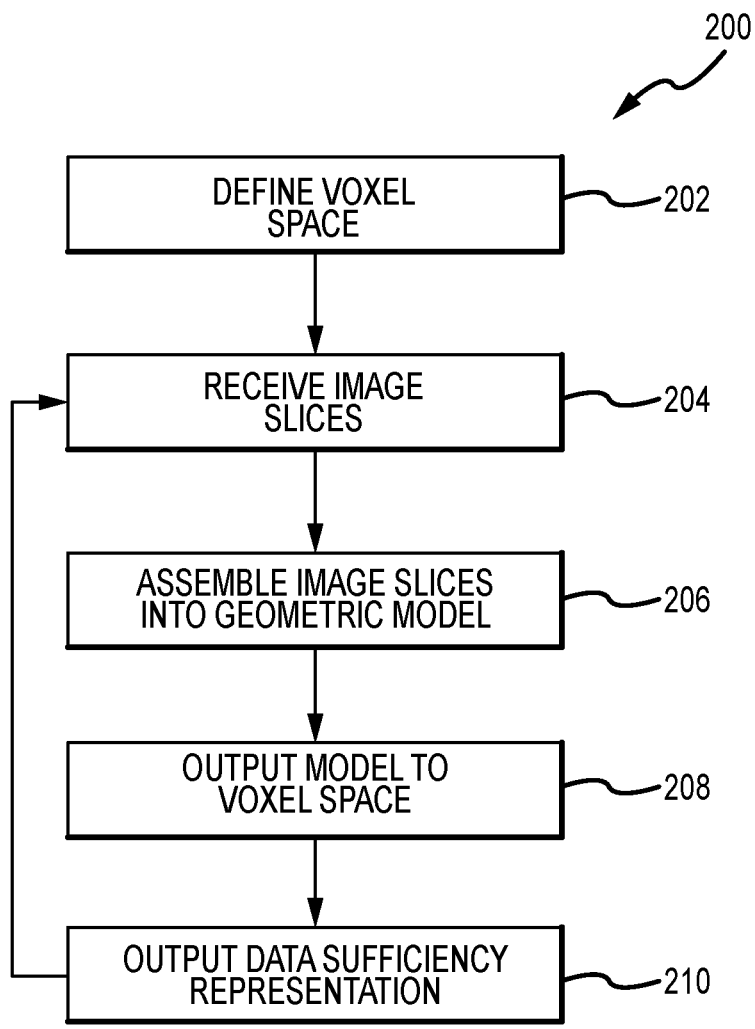
FIG. 2 is a flowchart of representative steps that can be followed according to exemplary embodiments disclosed herein.

One exemplary method of generating a three-dimensional geometric model according to the present teachings will be explained with reference to the flowchart 200 of representative steps presented as FIG. 2. In some embodiments, for example, flowchart 200 may represent several exemplary steps that can be carried out by system 8 of FIG. 1 (e.g., by processor 28 and/or imaging and modeling module 58). It should be understood that the representative steps described below can be either hardware- and/or software-implemented.

In block 202, system 8 defines a three-dimensional voxel space including a plurality of voxels. This voxel space provides an environment within which to visualize the three-dimensional geometric model generated by system 8.

In block 204, system 8 receives a plurality of two-dimensional image slices of the heart from ICE catheter 13. Those of ordinary skill in the art will be familiar with echographic imaging modalities, such as B-mode ultrasound and color Doppler echocardiography, that are suitable for use in acquiring the image slices in block 204.

Because, in some embodiments, catheter 13 incorporates sensor 17, each two-dimensional image slice can also be associated with localization information. That is, each image slice can be associated with a particular position and orientation of catheter 13. In turn, system 8 (e.g., module 58) can assemble the plurality of two-dimensional image slices into a three-dimensional geometric model in block 206 according to their associated localization information.

In embodiments of the disclosure, system 8 can utilize information in addition to the associated localization information when assembling the two-dimensional image slices into the three-dimensional geometric model. For example, it is contemplated that the collection of two-dimensional image slices can be gated to the patient's EKG signal and/or respiration, such that all two-dimensional image slices that make up a particular three-dimensional model are from common cardiac and/or respiration phase(s).

As another example, system 8 can utilize parameters such as depth, frame rate, beam width, and the like when assembling the two-dimensional image slices into the three-dimensional geometric model.

In general, however, techniques for assembling two-dimensional echographic image slices into a three-dimensional geometric model will be familiar to the ordinarily skilled artisan (see, e.g., United States patent application publication no. 2012/0165664, which is hereby incorporated by reference as though fully set forth herein), and thus need not be discussed in further detail herein.

In block 208, system 8 outputs (e.g., to display 23) a graphical representation of the three-dimensional geometric model in the three-dimensional voxel space. For instance, system 8 can utilize the localization information associated with the two-dimensional image slices to map ICE imagery to corresponding voxels within the voxel space.

In block 210, system 8 outputs (e.g., to display 23) a graphical representation of the data sufficiency of the three-dimensional geometric model created in block 206. By way of further explanation, when creating a three-dimensional geometric model, it is desirable that the imagery collected by catheter 13 uniformly cover the entirety of the region of interest, without holes or gaps, including exhibiting consistency with respect to cardiac and/or respiratory phase. In this disclosure, the term "data sufficiency" refers to such coverage.

In some embodiments of the disclosure, data sufficiency is illustrated concurrent with the three-dimensional geometric model within the three-dimensional voxel space (referred to herein as a "three-dimensional illustration of data sufficiency"). For instance, each voxel within the voxel space can have an opacity value that varies directly with data sufficiency at that voxel. Thus, voxels having more image data will appear more opaque on display 23, voxels having less image data will appear less opaque on display 23, and voxels having little or no image data will be transparent, and thus not visible on display 23. This allows a practitioner to quickly identify where additional image data should be collected, for instance because catheter 13 never collected image data for certain locations and/or because the image data collected by catheter 13 for certain locations did not match other image data as to cardiac and/or respiratory cycle.

To be clear, the term "data sufficiency" refers to the availability of suitable image data at a given voxel. "Data sufficiency" does not necessarily relate to the pixel intensity of a given pixel in a two-dimensional echographic image slice.

Figure 3A:
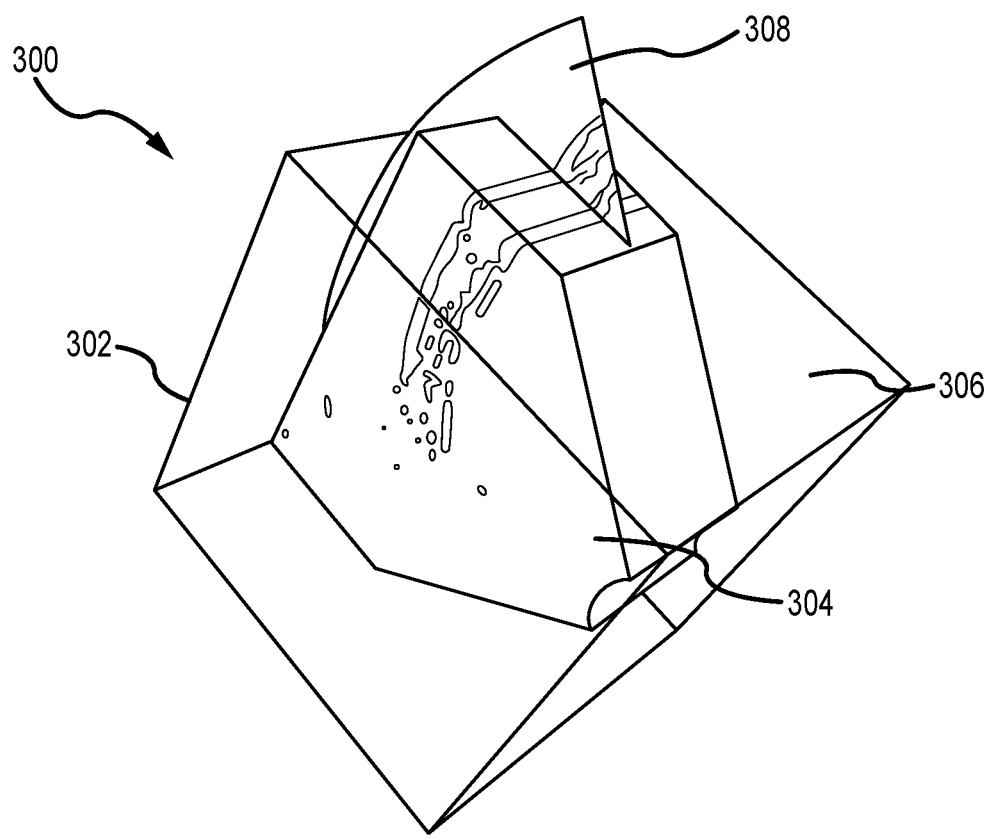
FIG. 3A is a representative three-dimensional illustration of data sufficiency according to aspects of the instant disclosure.

FIG. 3A depicts a representative three-dimensional illustration 300 of data sufficiency according to the foregoing disclosure. The voxel space is shown as a box 302. Opaque voxels 304 reflect the presence of image data from catheter 13, while transparent voxels 306 reflect the absence of image data from catheter 13 (for reference, a single two-dimensional image slice 308 is also shown).

Figure 3B:
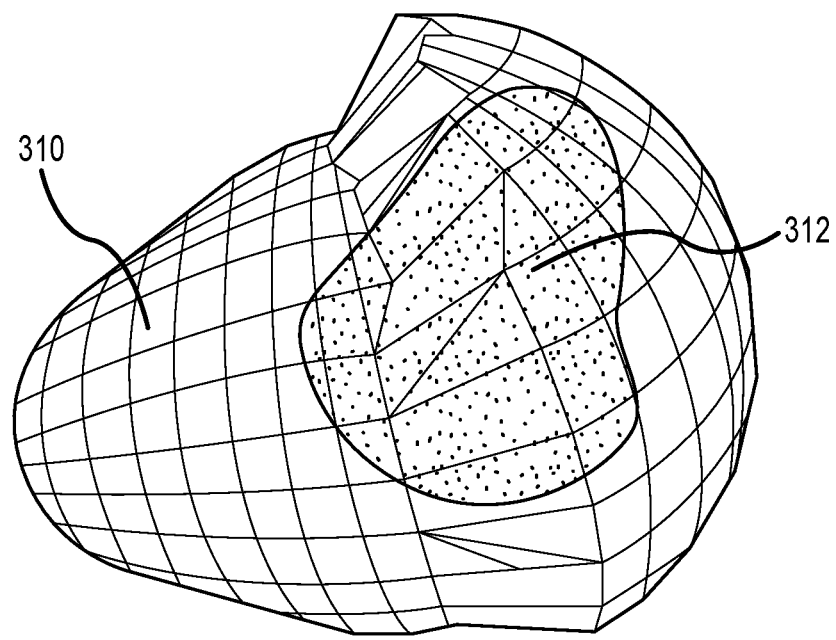
FIG. 3B is a representative three-dimensional geometric model that incorporates an illustration of data sufficiency according to aspects of the instant disclosure.

Within the opaque voxels, voxel color corresponds to density (e.g., as measured using images collected by catheter 13), with higher density areas (e.g., cardiac wall) depicted in a dark color, such as grey, and lower density areas (e.g., blood) depicted in a brighter color, such as yellow. Thus, as shown in FIG. 3B, the opaque, brighter-colored surface 310 shows the entire scanned region, while the opaque, darker-colored surface 312 shows the higher-density cardiac surface.

Figure 4:
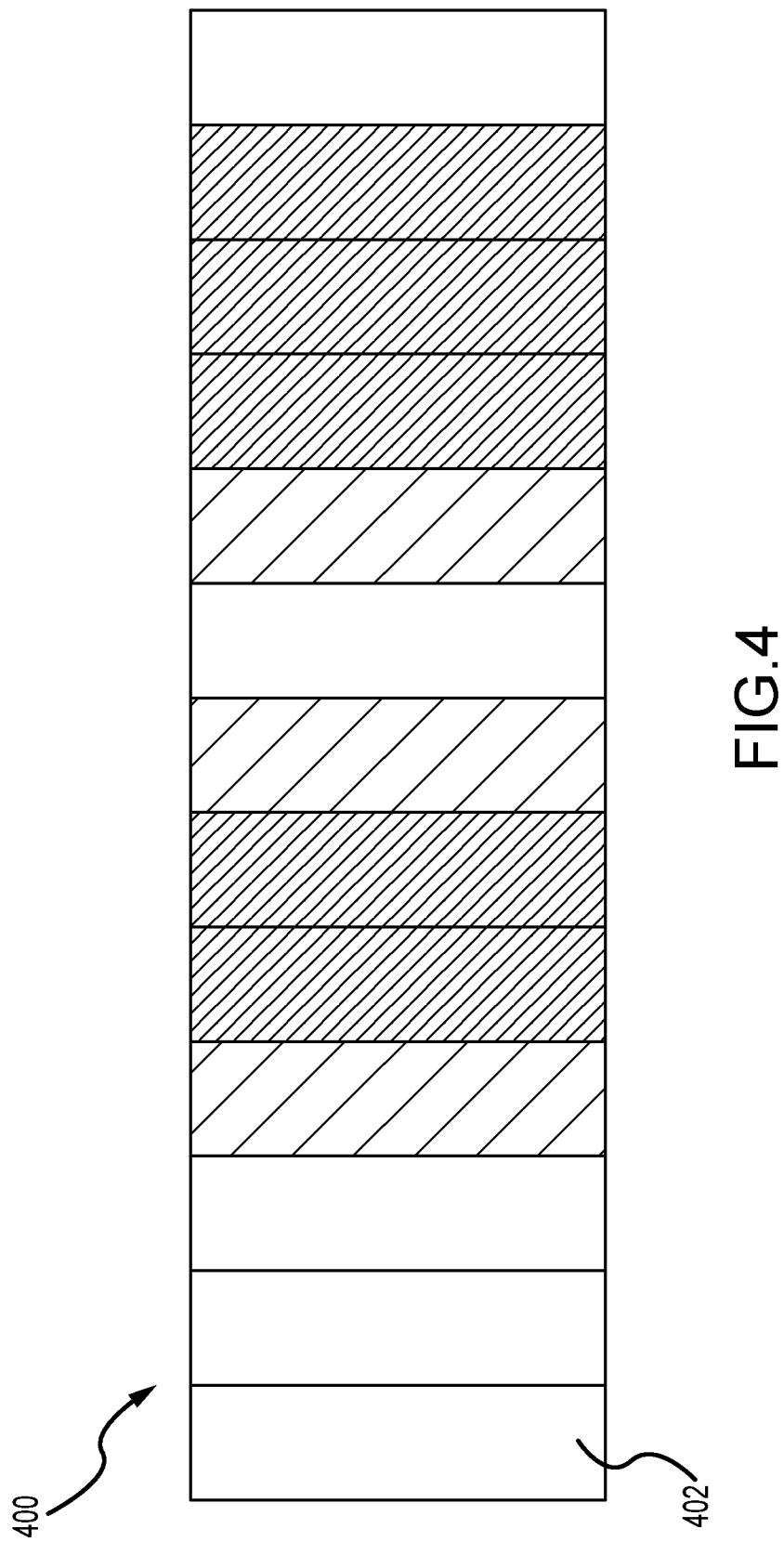
FIG. 4 is a representative one-dimensional illustration of data sufficiency according to aspects of the instant disclosure.

Another approach to graphically representing data sufficiency, referred to herein as a "one-dimensional illustration of data sufficiency," is depicted in FIG. 4. Because typical ICE catheters transmit their ultrasound beams laterally, it is common to image a region by rotating an ICE catheter about its longitudinal axis ("roll"). Data sufficiency, therefore, can be expressed relative to the roll angle of the ICE catheter (that is, relative to a single degree of freedom).

FIG. 4 depicts a bar-shaped one-dimensional data sufficiency indicator 400. Each bin 402 of indicator 400 represents a range of ICE catheter roll orientations, and the color or shading within each bin 402 represents data sufficiency within that range. For instance, a bin 402 can transition from red to yellow to green or gradually shade darker as data sufficiency improves. This allows a practitioner to quickly identify what roll orientations still need to be imaged.

It should also be understood that, although FIG. 4 depicts 13 bins 402, any number of bins 402 can be used without departing from the scope of the instant disclosure. Indeed, as more bins 402 are included, the range of roll orientations represented by each bin narrows, allowing for a more detailed understanding of where additional imagery should be captured.

Further, because indicator 400 only expresses data sufficiency with respect to a single degree of freedom (e.g., roll), it can be invalidated if catheter 13 experiences significant displacement on any other degree(s) of freedom (e.g., if catheter 13 translates or deflects). Although system 8 may be able to compensate for some such displacements, it is also contemplated that indicator 400 can be updated or reset (e.g., green-colored or fully-shaded bins 402 can be reset to red-colored or unshaded) should such a displacement occur.

Figure 5:
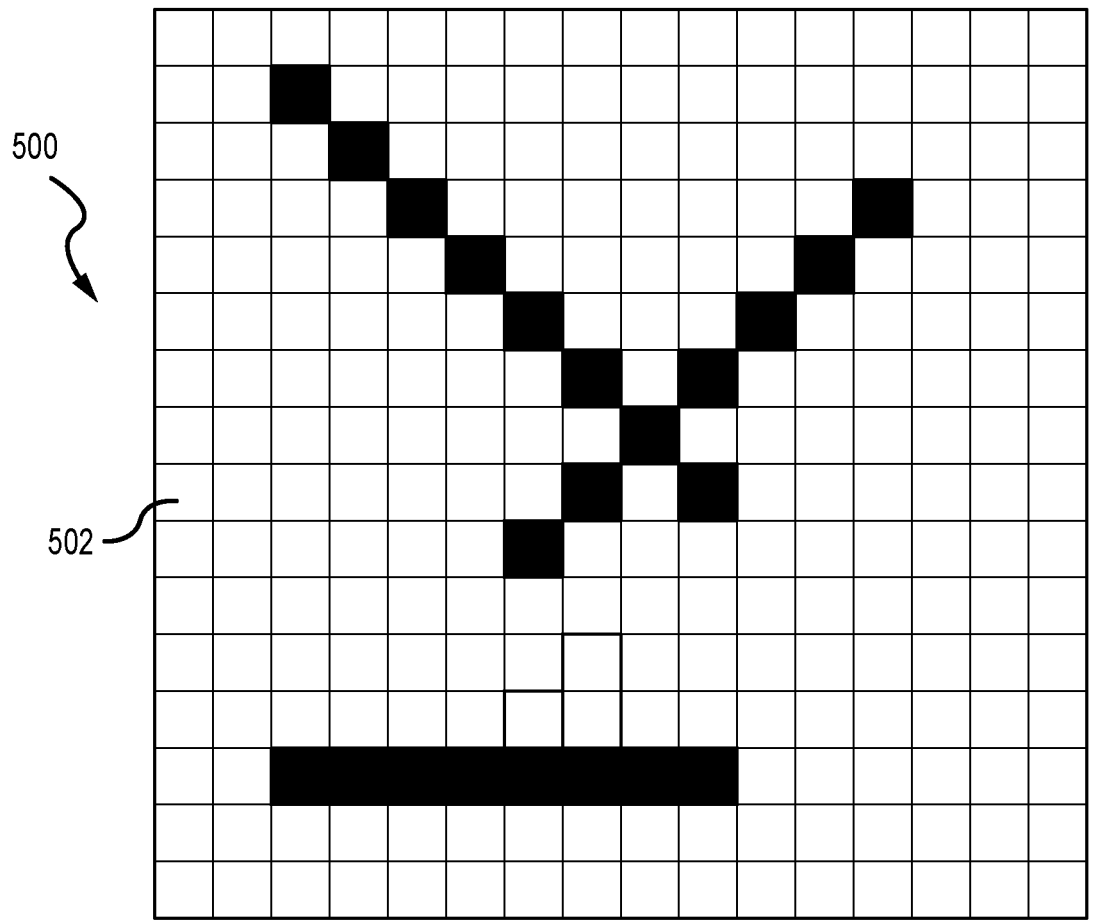
FIG. 5 is a representative two-dimensional illustration of data sufficiency according to aspects of the instant disclosure.

In still other aspects of the disclosure, a two-dimensional illustration of data sufficiency can be used. FIG. 5 depicts an exemplary two-dimensional indicator 500 of data sufficiency that represents data sufficiency as a function of both position and orientation of catheter 13. More particularly, indicator 500 projects the three-dimensional voxel space onto a two-dimensional array of pixels 502. Similar to the voxel opacity approach to illustrating data sufficiency described above, the coloration and/or shading of each pixel 502 can be dependent on data sufficiency at that pixel.

In further aspects of the disclosure, the data sufficiency representation output in block 210 also includes a data collection cue. As used herein, the term "data collection cue" refers to a cue that relates the motion of catheter 13 to data collection. For instance, a heart chamber cannot be imaged in a single, 360-degree rotation of catheter 13 if the roll speed of catheter 13 is too fast. System 8 can therefore output a cue that informs the practitioner to slow down as necessary. The cue can be visual (e.g., a flashing or colored indicator on display 23), audible (e.g., a tone that sounds if catheter 13 is rolling too fast), haptic (e.g., a vibration in the handle of catheter 13 if it is rolling too fast), or a combination thereof.

The data sufficiency representation output in block 210 can be interpreted by the practitioner in a manner that allows the practitioner to identify additional image slices, thereby improving data sufficiency within at least a portion of the geometric model. Alternatively or additionally, system 8 can output guidance, in the form of visual, audible, and/or haptic feedback, that guides the practitioner to move catheter 13 to regions where data sufficiency is relatively lower in order to collect additional image slices and thereby improve data sufficiency within a corresponding portion of the geometric model.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to imagery collected during an electrophysiology study performed at an earlier time).

As another example, although a bar-shaped data sufficiency indicator is one representative one-dimensional illustration of data sufficiency, other shapes are contemplated. For instance, data sufficiency can also be expressed via a pie-shaped data sufficiency indicator divided into a plurality of wedges that each depict data sufficiency over a range of catheter roll orientations.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating a three-dimensional geometric model of an anatomical region, the method comprising:
    defining a three-dimensional voxel space comprising a plurality of voxels; receiving a plurality of two-dimensional echographic image slices of the anatomical region, wherein each image slice of the plurality of image slices is associated with localization information;
    assembling the plurality of two-dimensional echographic image slices of the anatomical region into a three-dimensional geometric model of the anatomical region using the associated localization information;
    graphically outputting the three-dimensional geometric model of the anatomical region in the three-dimensional voxel space; and
    graphically representing data sufficiency of the three-dimensional geometric model of the anatomical region, wherein graphically representing data sufficiency of the three-dimensional geometric model of the anatomical region comprises outputting a one-dimensional illustration of the data sufficiency of the three-dimensional geometric model.

2. The method according to claim 1, further comprising outputting guidance to a practitioner to increase data sufficiency of at least a portion of the three-dimensional geometric model.

3. The method according to claim 1, wherein graphically representing data sufficiency of the three-dimensional geometric model of the anatomical region comprises representing the data sufficiency of the three-dimensional geometric model of the anatomical region using voxel opacity.

4. The method according to claim 3, wherein, for a selected voxel of the plurality of voxels, an opacity of the selected voxel increases as data sufficiency at the selected voxel increases.

5. The method according to claim 1, wherein the one-dimensional illustration of the data sufficiency of the three-dimensional geometric model represents data sufficiency of the three-dimensional geometric model relative to angular orientation of the plurality of echographic image slices.

6. The method according to claim 1, wherein graphically representing data sufficiency of the three-dimensional geometric model of the anatomical region comprises outputting a two-dimensional illustration of the data sufficiency of the three-dimensional geometric model.

7. The method according to claim 6, wherein the two-dimensional illustration of the data sufficiency of the three-dimensional geometric model represents data sufficiency of the three-dimensional geometric model relative to localization of the plurality of echographic image slices.

8. The method according to claim 1, wherein graphically representing data sufficiency of the three-dimensional geometric model of the anatomical region comprises outputting a data collection cue.

9. A method of generating a three-dimensional geometric model of a heart, the method comprising:
receiving a plurality of two-dimensional image slices of the heart from an intracardiac echocardiography ("ICE") catheter, wherein each image slice of the plurality of image slices is associated with localization information of the ICE catheter;
graphically outputting the plurality of two-dimensional image slices in a plurality of voxels according to the associated localization information of the ICE catheter, thereby creating a three-dimensional geometric model of the heart; and
graphically representing data sufficiency of the three-dimensional geometric model of the heart, wherein graphically representing data sufficiency of the three-dimensional geometric model of the heart comprises one or more of:
representing data sufficiency of the three-dimensional geometric model of the heart using a one-dimensional illustration of data sufficiency relative to angular rotation of the ICE catheter; and
representing data sufficiency of the three-dimensional geometric model of the heart using a two-dimensional illustration of data sufficiency relative to localization of the ICE catheter.

10. The method according to claim 9, wherein graphically representing data sufficiency of the three-dimensional geometric model of the heart further comprises representing data sufficiency at a selected voxel of the plurality of voxels using opacity of the selected voxel.

11. The method according to claim 9, wherein graphically representing data sufficiency of the three-dimensional geometric model of the anatomical region further comprises outputting a data collection cue.

12. The method according to claim 11, wherein the data collection cue is responsive to a rotational speed of the ICE catheter.

13. A system for generating a three-dimensional geometric model of a heart, comprising:
an imaging and modeling module configured to:
receive a plurality of two-dimensional image slices of the heart from an intracardiac echocardiography ("ICE") catheter, wherein each image slice of the plurality of image slices is associated with localization information of the ICE catheter;
graphically output the plurality of two-dimensional image slices in a plurality of voxels according to the associated localization information of the ICE catheter, thereby creating a three-dimensional geometric model of the heart; and
graphically represent data sufficiency of the three-dimensional geometric model of the heart, wherein the imaging and modeling module is configure to graphically represent data sufficiency of the three-dimensional geometric model of the heart using one or more of voxel opacity, a one-dimensional illustration, and a two-dimensional illustration.

14. The system according to claim 13, wherein the imaging and modeling module is further configured to graphically represent data sufficiency of the three-dimensional geometric model of the heart using a data collection cue.

15. The system according to claim 13, wherein the imaging and modeling module is configured to output guidance to a practitioner to increase data sufficiency of at least a portion of the three-dimensional geometric model of the heart.

* * * * *